United States Patent
Goto et al.

(10) Patent No.: US 6,344,207 B1
(45) Date of Patent: *Feb. 5, 2002

(54) MOLDED ANTIMICROBIAL ARTICLE AND A PRODUCTION PROCESS THEREOF

(75) Inventors: Hirotoshi Goto, Tokyo; Masaki Ishii; Koichi Saito, both of Shiga, all of (JP)

(73) Assignee: Toray Industries, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,199

(22) Filed: Apr. 23, 1999

(30) Foreign Application Priority Data

Apr. 24, 1998 (JP) .......................................... 10-115162

(51) Int. Cl.⁷ ............................................. A01N 25/34
(52) U.S. Cl. ...................... 424/404; 424/402; 424/405; 424/406; 424/443; 428/357
(58) Field of Search ................................ 424/404, 405, 424/406, 443; 428/357

(56) References Cited

U.S. PATENT DOCUMENTS

| | | | |
|---|---|---|---|
| 4,343,853 A | * | 8/1982 | Morrison ..................... 428/233 |
| 4,424,060 A | | 1/1984 | Shinichi et al. .............. 8/115.5 |
| 4,663,365 A | * | 5/1987 | Reinehr et al. ............. 523/122 |

FOREIGN PATENT DOCUMENTS

| | | | |
|---|---|---|---|
| JP | 61 239082 A | | 10/1986 |
| JP | 61-239082 | * | 10/1986 |
| JP | 61 282475 A | | 12/1986 |
| JP | 61-282475 | | 12/1986 |
| JP | 4-66505 | | 3/1992 |
| JP | 04 082962 A | | 3/1992 |
| JP | 9-273073 | | 10/1997 |
| JP | 09 273073 A | | 10/1997 |

* cited by examiner

*Primary Examiner*—Jose' G. Dees
*Assistant Examiner*—Konata M. George
(74) *Attorney, Agent, or Firm*—Schnader Harrison Segal & Lewis LLP

(57) ABSTRACT

The invention relates to a molded antimicrobial article including an infiltrated antimicrobial agent which forms independent phases of 0.01 $\mu$m or more in short diameter in the molded article. The antimicrobial agent is a pyridine based antimicrobial agent with a molecular weight of 200 to 700 and an inorganic property/organic property value of 0.3 to 1, and 50% or more of the antimicrobial agent is infiltrated in a depth range of 0.5 $\mu$m or more from the surface of the molded article, or that 30% or more of the antimicrobial agent is infiltrated in a depth range of 2 $\mu$m or more from the surface of the molded article. The molded antimicrobial article of the invention can be obtained by immersing a fibrous product in a dyeing liquid containing the pyridine based antimicrobial agent, and treating simultaneously with dye under pressurization, or by applying a liquid containing a pyridine based antimicrobial agent to a fibrous product by padding or spraying, and heat-treating it at 160 to 200° C. in a dry or wet state.

21 Claims, No Drawings

MOLDED ANTIMICROBIAL ARTICLE AND A PRODUCTION PROCESS THEREOF

TECHNICAL FIELD

The present invention relates to molded antimicrobial articles, particularly antimicrobial fibers excellent in industrial washing durability, and a production process thereof.

BACKGROUND

Molded antimicrobial articles, especially fibers, are widely used for various clothes, interlinings, linings, bedclothes, interior products and the like. These fibrous products are excellent in antimicrobial activity and, by various improvements, have become good in household water washing durability.

However, in recent years, occurrences of infection in hospitals due to methicillin resistant Staphylococcus (MRSA) has become a problem. As a countermeasure, white overalls, covers, sheets, curtains and the like have been treated in an attempt to impart antimicrobial characteristics. However, these fibrous products for use in hospitals are usually very frequently industrially washed at 60 to 85° C., and few conventional techniques provide sufficient durability against such washing.

Fibers have been treated to impart antimicrobial characteristics by blending an inorganic antimicrobial agent such as silver, copper or zinc into synthetic fibers at the spinning stage, or by applying an organic antimicrobial agent such as a quaternary ammonium salt by spraying or padding in a post-treatment. The former method is excellent in view of washing durability, but does not permit antimicrobial treatment at a later stage. Furthermore, the antimicrobial agent precipitates as crystals on the spinneret face during spinning to cause frequent fiber breaking and the like, which is a problem in the yarn production process. On the other hand, the latter method is poor in washing durability of antimicrobial activity, although it advantageously allows antimicrobial treatment in a later stage.

JP-A-61-239082 describes treating N6 socks in a pyridine based antimicrobial agent suspension at 130° C. for 60 minutes with shaking. However, when a suspension is used, the particle size of the antimicrobial agent is too large to obtain a sufficient effect. Furthermore, JP-A-09-273073 describes treating polyester fibers with a pyridine based antimicrobial agent simultaneously with dyeing, but the antimicrobial agent used is not proper and does not provide a sufficient effect.

Accordingly, it is highly desirable to provide a molded antimicrobial fibrous product excellent in industrial washing durability and a production process thereof.

SUMMARY OF THE INVENTION

The present invention relates to a molded antimicrobial article, comprising an infiltrated antimicrobial agent which forms independent phases of 0.01 $\mu$m or more in short diameter in the molded article. It is preferable that a pyridine based antimicrobial agent with a molecular weight of about 200 to about 700 and an inorganic property/organic property value of about 0.3 to about 1.4 forms independent phases of about 0.01 $\mu$m or more in short diameter in the molded article, and that about 50% or more of the antimicrobial agent is infiltrated to a depth range of about 0.5, preferably, about 1 $\mu$m or more from the surfaces of fibers, or about 30% or more of the antimicrobial agent is infiltrated to a depth range of about 2 $\mu$m or more from the surfaces of fibers. It is also preferable that the molded articles are fibers, that the surface area used per 1 g of fibers is about 0.1 $m^2$ or more, and that the synthetic fibers are a colored antimicrobial fibrous product.

The molded antimicrobial article of the invention can be obtained, for example, by immersing a fibrous product in a dyeing liquid containing a pyridine based antimicrobial agent with a molecular weight of about 200 to about 700, an inorganic property/organic property value of about 0.3 to about 1.4 and an average particle size of about 2 $\mu$m or less and, preferably, treating simultaneously with dyeing under pressurization.

As another embodiment, the antimicrobial article can also be obtained by applying a liquid containing the same pyridine based antimicrobial agent to a fibrous product by padding or spraying, and heat-treating at about 160 to 200° C. in a dry or wet state.

DETAILED DESCRIPTION OF THE INVENTION

It will be appreciated that the following description is intended to refer to specific embodiments of the invention selected for illustration and is not intended to define or limit the invention, other than in the appended claims.

A preferable antimicrobial agent used in the present invention has a molecular weight of about 200 to about 700, an inorganic property/organic property value of about 0.3 to about 1.4 and an average particle size of about 2 $\mu$m or less.

A pyridine based antimicrobial agent is stably infiltrated and diffused into a molded article, especially synthetic fibers and synthetic resin films. The molded article can also be of any other form such as a film, sheet, plate or rod. However, for the sake of simplicity, this description is limited to cases of fibers. We have discovered that the antimicrobial agent dispersed in the molded article shows behavior similar to that of the disperse dye if the antimicrobial agent is particularly selected to be closer to the disperse dye in three requirements: molecular weight, inorganic property/organic property value and average particle size.

However, it is surprising that the solid antimicrobial agent forms independent phase of about 0.01 $\mu$m or more in "short diameter" inside the fibers, and that about 50% or more of the antimicrobial agent is infiltrated to a depth range of about 0.5, preferably, about 1 $\mu$m or more from the surfaces of the fibers or that about 30% or more of it is infiltrated to a depth range of about 2 $\mu$m or more from the surfaces of the fibers. "Short diameter" as used herein means the number average diameter of independent phases taken through a cross section of the fiber.

It is not clearly understood that the antimicrobial agent can be diffused as particles in the highly crystalline and structurally dense fibers. However, without being bound by any particular theory, we believe that the antimicrobial agent is dispersed as, respectively, single molecules or groups consisting of several cohesive molecules, to be precipitated which forms independent phases of agent in the particles in the fibers. As for the diffusion degree of the antimicrobial agent, if the distance from the fiber surface to the center of the fiber section is set at 1, the antimicrobial agent is infiltrated and diffused into the fiber at least a distance of about 0.2. As for the concentration distribution of the antimicrobial agent, the ratio of the concentration of the antimicrobial agent existing in a range from the center of the fiber section to a distance nearest to the center of the fiber section to the concentration of the antimicrobial agent existing in a range from the center of the fiber section to the surface is about 1:1 to about 1:10. Thus, the antimicrobial agent is sufficiently infiltrated inside the fibers. Unless these conditions are satisfied, the antimicrobial agent is not properly diffused into the synthetic fibers, and sufficient industrial washing durability cannot be obtained.

Washing durability is low if the molecular weight of the antimicrobial agent is less than about 200, even when the antimicrobial agent is infiltrated and diffused into the synthetic fibers. On the other hand, the antimicrobial agent is not infiltrated into the synthetic fibers if its molecular weight is more than about 700. It is preferable that the molecular weight of the antimicrobial agent is about 300 to about 500.

The "inorganic property/organic property value" referred to in the invention is a value defined by Minoru Fujita for expressing the polarity of various organic materials [Revised Edition, Science of Chemical Experiments—Organic Chemistry—Kawade Shobo (1971)]. Specifically, it is a ratio of the sum of inorganic property values to the sum of organic property values obtained from the inorganic property values and organic property values of various polar groups shown in Table 1 with the organic property value of one carbon atom as 20.

For example, 2,3,5,6-tetrachloro-4-hydroxypyridine has an inorganic property value of 265 since it has one benzene nucleus, four—Cl groups, one—OH group and one—NR group, and has an organic property value of 180 since it has five carbon atoms and four—Cl groups. Hence the inorganic property/organic property value of the compound is 1.47. Furthermore, 2-pyridylthiol-1-oxide zinc exists as a chelate complex, and judging from its electronegativity, it is considered that zinc and sulfur form a covalent bond. Thus, the compound has an inorganic property value of 85 and an organic property value of 190 and, hence, an inorganic property/organic property value of 0.45, according to the calculation method.

On the other hand, in the case of 2-pyridylthiol-1-oxide sodium, which is also a pyridine based antimicrobial agent, since the electronegativity difference between sodium and sulphur is more than 1.6, the bond is an ionic bond. In this case, sodium acts as a light metal salt. Thus, the compound has an inorganic property value of 585 and an organic property value of 190 and, hence, an inorganic property/organic property value of 3.0, according to the calculation method. It is poor in affinity to polyesters.

It is preferable that the antimicrobial agent has an average particle size of about 2 μm or less. The antimicrobial agent

TABLE 2

| Inorganic group | Value | Inorganic Group | Value | |
|---|---|---|---|---|
| Light metal salt | >500 | >CO | 65 | |
| Light metal salt, amine or ammonium salt | >400 | —COOR, —P=P— | 60 | |
| —ASO$_3$H, —AOS$_2$H | 300 | >C=NH | 50 | |
| —So$_2$NHCO—, —N=N—NH$_2$ | 260 | —N=N— | 30 | |
| —SO$_3$H, —CONHCONHCO— | 250 | >O | 20 | |
| —SO$_2$NH—, CONHCONH— | 240 | Benzene nucleus (general aromatic single nucleus) | 15 | |
| —CONHCO—, CSNH— | 230 | Non-aromatic ring | 10 | |
| =NOH | 220 | Triple bond | 3 | |
| =N—NH— | 210 | Double bond | 2 | |
| —COHN— | | Organic and Ingorganic Group | Organic Property Value | Inorganic Property Value |
| —CSSH | 180 | >SO$_2$ | 40 | 110 |
| —CSOH, —COSH | 160 | —SCH | 70 | 80 |
| Anthracene nucleus or phenanthrene nucleus | 155 | —NCS | 70 | 75 |
| —COOH | 150 | —NO$_2$ | 70 | 70 |
| Lactone | 120 | —CN | 40 | 70 |
| —CO—O—CO— | 110 | —NO | 50 | 50 |
| —OH, —As—O—As— | 100 | —ONO$_2$ | 60 | 40 |
| —Hg (organic) | 95 | —NC | 40 | 40 |
| —COSR, —CSOR, —AS=AS— | 90 | —NCO | 30 | 30 |
| Naphthalene nucleus | 85 | -1 | 60 | 20 |
| —NH—NH—, —O—CO—O— | 80 | —Br, —SH, —S— | 40 | 20 |
| —NH$_2$, —NHR, —NR$_2$ | 70 | —CI, —P | 20 | 20 |

Note:
Each carbon atom in the above inorganic groups is counted as 20 in organic property value. However, the values of SO$_2$ and others are counted in the organic property values of organic and inorganic groups.

The inorganic property/organic property value of polyethylene terephthalate calculated according to this method is 0.7. The affinity between synthetic fibers and the antimicrobial agent based on the value calculated according to this method, and an antimicrobial agent with the inorganic property/organic property value kept in the predetermined range is sufficiently infiltrated and diffused in the synthetic fibers.

If the inorganic property/organic property value is less than about 0.3, the organic property is too strong, and if more than about 1.4, the inorganic property is so strong that the antimicrobial agent is less likely to be infiltrated and diffused into the synthetic fibers. It is preferable that the inorganic property/organic property value is in a range of about 0.35 to about 1.3, more preferably from about 0.4 to about 1.2.

is less likely to be infiltrated and diffused into the synthetic fibers if the average particle size is more than about 2 μm, and when the antimicrobial agent is provided as an aqueous liquid, the particles precipitate. Hence, the liquid tends to be poor in stability. It is preferable that the average particle size of the antimicrobial agent is about 1 μm or less.

The antimicrobial agents which can be used in the invention include, but are not limited to, pyridine based compounds such as 2-chloro-6-trichloromethylpyridine, 2-chloro-4-trichloromethyl-6-methoxypyridine, 2-chloro-4-trichloromethyl-6-(2-furylmethoxy)pyridine, di(4-chlorophenyl)pyridylmethanol, 2,3,5-trichloro-4-(n-propylsulfonyl)pyridine, 2-pyridylthiol-1-oxide zinc, and di(2-pyridylthiol-1-oxide). Among them, 2-pyridylthiol-1-oxide zinc is especially good in affinity to fibers, and is stably filtrated into the fibers. It has good washing durability and is also preferable in view of the variety of microbial strains including MRSA against which it is effective.

The materials of the synthetic fibers which can be used as the fibrous product of the invention can be polyesters, acrylic resins, nylons and the like. The fibrous product of the invention can also be natural fibers of cotton, wool or silk and the like, in addition to those synthetic fibers, or a combination with semi-synthetic fibers such as rayon, as yarns, woven fabric or nonwoven fabric and the like. Among such synthetic fibers, polyester fibers can provide a fibrous product most excellent in industrial washing durability of antimicrobial activity.

Furthermore, in the invention, the fibers can be colored. In other words, the fibers may contain a colorant such as disperse dye, acid dye, cationic dye or fluorescent whitening agent.

In considering antimicrobial activity, depositing the antimicrobial agent on the surfaces of fibers is most preferred since the frequency of contact with bacteria is high. However, in this state, the antimicrobial agent is likely to be removed and, accordingly, washing durability is not good. On the other hand, if the antimicrobial agent is diffused into the fibers and forms independent phases within the particles of about 0.01 $\mu$m or more in short diameter inside the fibers, washing durability is high, although the antimicrobial activity is not as high.

With regard to washing durability, it is preferable that the size of the antimicrobial agent in the fibers is about 0.02 $\mu$m or more in short diameter. Although a larger size such as about 0.5 $\mu$m or about 1 $\mu$m can be effective, the size of the independent phases is preferably about 0.02 to about 0.5 $\mu$m in short diameter. Typically, it is about 0.02 to about 0.2 $\mu$m. For these reasons, it can be considered to be excellent in view of both antimicrobial activity and washing durability that the antimicrobial agent is distributed substantially annularly near the surface of each fiber inside the fiber, or diffused like branches from the surface of each fiber into the inside, or distributed as "lumps" inside each fiber. This distribution may be random, uniform or otherwise.

The concentration distribution of the antimicrobial agent inside each fiber can be easily confirmed by analyzing a section of the fiber using an X-ray microanalyzer (EMAX-2000 produced by Horiba Seisakusho), and evaluating the concentration distribution of any specific element such as sulfur contained in the antimicrobial agent inside the fiber.

The state where the antimicrobial agent forms independent phases of about 0.01 $\mu$m or more in short diameter inside each fiber, the state where it is distributed substantially annularly near the surface of each fiber, the state where it is diffused like branches from the surface to inside of each fiber inside the fiber, or the state where it is distributed as lumps inside each fiber can be confirmed by observation with a scanning electron microscope (SEM).

The concentration distribution of the antimicrobial agent inside each fiber can be controlled into several states by changing the processing conditions into the state where the microbial agent is deposited on the surface of each fiber, into the state where it is distributed substantially annularly in a range from the surface to the inside of each fiber, into the state where it is diffused like branches inside each fiber, or into the state where it is distributed as lumps inside each fiber.

It is also preferable that the microbiostatic activity value measured according to the microbe control evaluation method (standard testing method) specified by SEK (Seni Seihin Shin-kinou Hyouka Kyougikai: New Function Evaluation Conference for Fiber Goods) is about 2.2 or more after 50 times of industrial washing treatment for 12 minutes/wash at 80° C. using a washing liquid containing a surfactant. It is more preferable that the same microbiostatic activity value is maintained even when the washing time is changed to 15 minutes/wash.

It is further preferable that the microbiostatic activity value is about 2.2 or more even if the washing treatment conditions are more severe. That is, it is further preferable that the same microbiostatic activity value is maintained even when a washing liquid containing a peroxide, strong alkali and surfactant was used. It is most preferable that the same microbiostatic activity value is maintained even when the washing time was changed to 15 minutes/wash and the washing liquid containing a peroxide, strong alkali and surfactant was used.

The washing liquid containing a peroxide, strong alkali and surfactant in this case is prepared, for example, by supplying 2 g/l of detergent "Zab" produced by Kao Corp., 3 cc/l of hydrogen peroxide water (35% industrial use) as a peroxide, and 1.5 g/l of sodium percarbonate as a strong alkali into a drum dyeing machine filled with water at a bath ratio of 1:20, and mixing them. The washing liquid is heated to 85° C., and an antimicrobial fibrous product of the invention and waste cloth are supplied into the liquid, for washing for 15 minutes. The machine is then drained, and the fibrous product is dewatered, washed by water with overflowing for 10 minutes, and finally dewatered. This washing is repeated 50 times, and the fibrous product is dried by a tumbler dryer for 20 minutes, for microbe control evaluation.

The process for producing the antimicrobial fibrous product of the invention is described below.

At first, a fibrous product is immersed in a liquid containing any of the pyridine based antimicrobial agents and a colorant such as a disperse dye, acid dye, cationic dye or fluorescent whitening agent in a jet dyeing machine, and heat-treated at atmospheric pressure or under pressurization at about 90 to about 160° C. It is preferable that the heat treatment time is about 10 to about 120 minutes. It is more preferable to heat-treat at about 120 to about 135° C. for about 20 to about 60 minutes. In this case, since the colorant and the pyridine based antimicrobial agent are heat-treated simultaneously in the liquid, the antimicrobial agent is deposited on the fibers and infiltrated and diffused inside the fibers like the dye. If the pyridine based antimicrobial agent is heat-treated in a bath at about 90 to about 160° C. after the fibrous product has been dyed, the colorant is desorbed from the fibers, not allowing the desired coloring to be achieved. On the other hand, if the fibers containing an antimicrobial agent are colored, the pyridine based antimicrobial agent is desorbed to lower the microbe control performance. If the heat treatment is effected at lower than about 90° C., the antimicrobial agent is not infiltrated in the synthetic fibers. If higher than about 160° C., the effect obtained is not high enough to be proportional to the energy consumption, thus lowering cost performance.

It is preferable that the fibrous product treated in the liquid according to the above method is treated by dry heat of about 160 to about 200° C., using a tenter dryer or the like. The treatment time can be about 15 seconds to about 5 minutes. It is more preferable that the dry heat treatment is effected at about 170 to about 190° C. for about 30 seconds to about 2 minutes. The dry heat treatment causes the antimicrobial agent to be diffused inside from the surfaces of the fibers, being distributed substantially annularly inside the fibers, or infiltrated and diffused like chains, to improve the washing durability without impairing the antimicrobial activity. If the heat treatment is effected at lower than about 160° C., the effect of dry heat treatment is less likely to be obtained. If higher than about 200° C., the fiber material is yellowed or becomes fragile, and the dye and the antimicrobial agent are sublimated or thermally decomposed while energy consumption increases. The respective states of adhesion of the antimicrobial agent can be controlled by changing the treatment conditions into being deposited on the surfaces of fibers, into substantially annular distribution inside the fibers or into diffusion inside the fibers.

As another embodiment of the process for producing the antimicrobial fibrous product of the invention, a liquid containing any of the pyridine based antimicrobial agents is applied to a colored fibrous product by padding or spraying, and the fibrous product is heat-treated in dry or wet state at about 160 to about 200° C. It is preferable that the heat treatment time is about 30 seconds to about 10 minutes. It is more preferable that the heat treatment is effected in a dry or wet state at about 170 to about 190° C. for about 2 to about 5 minutes. If the heat treatment temperature is lower than about 160° C., the pyridine based antimicrobial agent is not infiltrated in the fibers. If higher than about 200° C., the fiber material is yellowed or becomes fragile and the dye and the antimicrobial agent are sublimated or thermally decomposed while the energy consumption increases.

It is preferable that the pyridine based antimicrobial agent is granulated in a colloidal state. If the antimicrobial agent is colloidal, it can be stably infiltrated and diffused in the fibers. Especially if it is made colloidal by water and a formalin condensation product, the antimicrobial agent becomes higher in dispersibility and can keep a good dispersed state, being good in affinity to the synthetic fibers.

EXAMPLES

The present invention is described below more concretely in reference to examples. The "%" and "parts" in the examples are "wt %" and "parts by weight" unless otherwise stated. The quality evaluation in the examples was effected according to the following methods.

(1) Washing Method

A fibrous product was washed in a drum dyeing machine containing 2 g/l of detergent "Zab" produced by Kao Corp., 3 cc/l of hydrogen peroxide water (35% industrial use) and 1.5 g/l of sodium percarbonate at 85±2° C. at a bath ratio of 1:20 for 15 minutes, and the machine was drained. The fibrous product was dewatered, washed by water with overflowing for 10 minutes and dewatered. This washing was repeated. Finally, the fibrous product was dried using a tumbler dryer for 20 minutes.

(2) Antimicrobial Activity Testing Method

The microbe control evaluation method (standard testing method) specified by SEK was adopted, and a clinically isolated MRSA strain was used. A bouillon suspension of said test strain was injected into a cloth sample, and cultured in a sealed container at 37° C. for 18 hours. The viable cell number in the sample was counted, and the decrement or increment from the planted viable cell number was obtained, to judge according to the following criterion.

When the decrement or increment expressed by $\log(B/C)$ at $\log(B/A) > 1.5$ was 2.2 or more, the antimicrobial activity was judged to be acceptable.

In the above formulae, A denotes the viable cell number of the strain obtained by diffusing and collecting it from a sample not treated by any antimicrobial agent immediately after inoculating the sample with the strain; B denotes the viable cell number of the strain obtained by diffusing and collecting it from a sample not treated by any antimicrobial agent after culturing the strain in the sample for 18 hours; and C denotes the viable cell number of the strain obtained by diffusing and collecting it from a sample treated by an antimicrobial agent after culturing the strain in the sample for 18 hours.

(3) Distribution of Antimicrobial Agent Inside Fibers (3-1) Confirmation of concentration distribution A section of a fiber was analyzed using an X-ray microanalyzer (EMAX-2000 produced by Horiba Seisakusho), and with attention paid to any specific element such as sulfur contained in the antimicrobial agent, the concentration distribution of the antimicrobial agent inside the fiber was evaluated.

(3-2) Confirmation of infiltration and diffusion

The deposition of an antimicrobial agent on the surface of a synthetic fiber, or the substantially annular distribution of it inside a synthetic fiber, or the state where it is branched and diffuses inside from the surface of a fiber, or the state where it was distributed as lumps was confirmed by observation with a scanning electron microscope (SEM).

Examples 1 to 4, and Comparative Examples 1 to 4 were conducted according to the following conditions.

The antimicrobial agents used in the examples and comparative examples were formed into colloids. 50 g of the antimicrobial agent used in any of the examples, 20 g of formalin condensation product of naphthalenesulfonic acid and 30 g of sodium lignosulfonate were formed into a slurry together with 300 g of water, and the slurry was wet-ground using glass beads to obtain a colloidal composition with an average particle size of 1 $\mu$m.

A cloth sample was prepared as follows. Polyethylene terephthalate filament yarns described below were used to prepare a tubular knitted fabric using a circular knitting machine.

A cloth sample was made antimicrobial according to the following method. A cloth sample was immersed in a liquid containing 1% owf of a colloidal antimicrobial agent made according to the above method, 2% owf of a disperse dye and 0.5 g/l of a level dyeing agent at a bath ratio of 1:10 and pH 5 and dyed at 130° C. for 60 minutes according to a conventional method using a high pressure dyeing tester. It was washed by water and dried at 170° C. for 2 minutes, to obtain an antimicrobial cloth sample.

The cloth samples and antimicrobial agents used in the respective examples and comparative examples are stated below.

Example 1

A knitted fabric of drawn 75-denier 72-filament polyethylene terephthalate yarns was used as the cloth sample, and 2-pyridylthiol-1-oxide zinc was used as the antimicrobial agent. The antimicrobial agent had an average particle size of 2 $\mu$m, and in the cloth treated by it, it was partially deposited on the surfaces of fibers and mostly infiltrated or branched to diffuse inside from the surfaces of fibers, mostly being distributed near the surface layers.

Example 2

A knitted fabric of falsely twisted 150-denier 48-filament polyethylene terephthalate yarns was used as the cloth sample, and 2-pyridylthiol-1-oxide zinc was used as the antimicrobial agent. The antimicrobial agent had an average particle size of 0.5 $\mu$m, and in the cloth treated by it, it was partially deposited on the surfaces of the fibers and mostly branched to diffuse inside the fibers, the branches being distributed near the centers of the sections.

Example 3

A knitted fabric of falsely twisted 75-denier 12-filament polyethylene terephthalate yarns was used as the cloth sample, and 2-chloro-6-trichloromethylpyridine was used as the antimicrobial agent. The antimicrobial agent had an average particle size of 1 $\mu$m, and in the cloth treated by it, it was partially deposited on the surfaces of the fibers and mostly branched to diffuse inside the fibers, the branches being distributed near the centers of the sections.

Example 4

A knitted fabric of falsely twisted 150-denier 48-filament polyethylene terephthalate yarns was used as the cloth sample, and 2-chloro-4-trichloromethyl-6-(2-furylmethoxy) pyridine was used as the antimicrobial agent. The antimicrobial agent had an average particle size of 0.5 $\mu$m, and in the cloth treated by it, it was partially deposited on the surfaces of fibers and mostly branched to diffuse inside the fibers, the branches being distributed near the centers of the sections.

Comparative Example 1

A cloth sample was treated as described in Example 1, except that the average particle size of the antimicrobial agent was 3 $\mu$m.

Comparative Example 2

A cloth sample was treated as described in Example 1, except that the dyeing (treatment) temperature was 85° C.

Comparative Example 3

A cloth sample was treated as described in Example 2, except that the antimicrobial agent was 2-pyridinethiol-1-oxide sodium.

Comparative Example 4

A cloth sample was treated as described in Example 2, except that the antimicrobial agent was 1,4-(1-diiodomethysulfonyl)benzene.

Examples 5 and 6 and Comparative Examples 5 and 6 were conducted according to the following conditions.

The same cloth sample as Example 1 was dyed with a disperse dye. To make the pre-dyed cloth sample antimicrobial, it was immersed in an aqueous liquid containing 15 g/l of any of the following colloidal antimicrobial agents made according to the above method, squeezed to 70 wt % of the solution based on the cloth weight by a mangle, dried by a tenter dryer at 120° C. for 2 minutes, and heated at 190° C. for 1 minute.

Example 5

A knitted fabric of 100-denier 48-filament polyethylene terephthalate yarns was used as the cloth sample, and 2-pyridylthiol-1-oxide zinc was used as the antimicrobial agent. The antimicrobial agent had an average particle size of 2 $\mu$m, and in the cloth treated by it, it was partially deposited on the surfaces of fibers and mostly infiltrated to be distributed annularly.

Example 6

A sample cloth was treated as described in Example 7, except that the average particle size of the antimicrobial agent was 0.5 $\mu$m. In the cloth treated by the antimicrobial agent, it was partially deposited on the surfaces of fibers and mostly infiltrated to be distributed as lumps.

Comparative Example 5

A sample cloth was treated as described in Example 5, except that the antimicrobial agent was methyl-6-(2-thiophenecarbonyl)-1H-2-benzimidazolecarbamate.

Comparative Example 6

A sample cloth was treated as described in Example 6, except that the antimicrobial agent was 5-chloro-2-methyl-4-isothiazoline.

Six samples of the examples and six samples of the comparative examples, total 12 samples, were evaluated for antimicrobial activity (MRSA) before washing and after 50 times of industrial washing. The results are shown in Table 2.

TABLE 2

| | Anitmicrobial Agent | | |
|---|---|---|---|
| | Name(molecular weight) | AverageParticle Size *1 | Inorganic/Organic *2 |
| Examples | | | |
| 1 | 2-pyridylthiol-1-oxide zinc | 2 $\mu$m | 0.45 |
| 2 | (317) | 0.5 $\mu$m | |
| 3 | 2-chloro-6-trichloromethylpyridine | 1 $\mu$m | 0.83 |
| 4 | 2-chloro-4-trichloromethyl-6-(2-furylmethoxy)pyridine (329) | 0.5 $\mu$m | 0.73 |
| 5 | 2-pyridylthiol-1-oxide zinc | 2 $\mu$m | 0.45 |
| 6 | (317) | 0.5 $\mu$m | |
| Comparati | | | |
| 1 | 2-pyridylthiol-1-oxide zinc | 3 $\mu$m | 0.45 |
| 2 | (317) | 0.5 $\mu$m | |

TABLE 2-continued

| | | | |
|---|---|---|---|
| 3 | 2-pyridythiol-1-oxide sodium (149) | 3 μm | 3.00 |
| 4 | 1,4-(1-diiodo-methylsulfonyl) benzene (738) | 2 μm | 0.66 |
| 5 | Methyl 6-(2-thiophenecarbonyl)-1H-2-benzimidazolecarbamate | 0.5 μm | 1.52 |
| 6 | 5-chloro-2-methyl-4-isothiazoline-3-one (150) | 0.5 μm | 1.34 |

| Treating conditions | | Infiltrated | Infiltrated and diffused state |
|---|---|---|---|
| method | Temp. | amount (wt %)*4 | State |
| In a dyeing bath *3 | 130° C. | 0.10 | Branched to diffuse from the surfaces to inside of fibers, being mainly distributed near the surface layers |
| | | 0.40 | Branched to diffuse from the surfaces to inside of fibers, the branches being distributed to the centers. |
| | | — | |
| Padding and curing | 180° C. | 0.15 | Annularly distributed. |
| | | 0.18 | Distributed as lumps here and there. |
| In a dyeing bath | 130° C. | 0.03 | Deposited on the surfaces of fibers, but little infiltrated inside the fibers. After industrial washing, the anti-microbial agent in the surface layers mostly fell off. |
| | 85° C. | <0.01 | |
| | 130° C. | <0.01 | |
| Padding and curing | 180° C. | — | |
| | | — | |

| | of antimicrobial agent in fibers | | | | Microbiostatic |
|---|---|---|---|---|---|
| Concentration | Diffusion | Shorter | Percentage of depth | | activity value |
| gradient ratio | degree | diameter *5 | 1 μm or more | 2 μm or more | *6 |
| 1:2 | 0.3 | 0.15 | 80% | 40% | 4.6(o) |
| 1:4 | 0.4 | 0.12 | 75% | 40% | 5.0(o) |
| 1:5 | 0.4 | 0.13 | 80% | 55% | 4.8(o) |
| 1:5 | 0.5 | 0.14 | 70% | 50% | 5.0(o) |
| 1:7 | 0.8 | 0.15 | 70% | 45% | 5.7(o) |
| 1:8 | 0.9 | 0.15 | 65% | 35% | 5.8(o) |
| 1:2 | 0.1 | unclear | 30% | 20% | 1.8(X) |
| 1:1 | 0.05 | No | 20% | 5% | 1.0(X) |
| 1:2 | 0.2 | independent | 40% | 25% | 1.2(X) |
| 1:1 | 0.05 | phase was | 15% | 10% | 1.8(X) |
| 1:1 | 0.2 | observed | 30% | 20% | 1.0(X) |
| 1:3 | 0.1 | | 35% | 15% | 1.9(X) |

*1: Number average
*2: Inorganic property/organic property value
*3: Simultaneously with dyeing
*4: Based on fiber weight and determined by HPLC analysis after carbonization
*5: Number average
*6: 2.2 or more after washing is acceptable As can be seen from Table 2, the samples of Examples 1 to 8 had sufficient antimicrobial activity before washing and also after 50 times of industrial washing. On the other hand, the samples of Comparative Examples 1 to 8 did not show any effect after 50 times of industrial washing, though some showed an antimicrobial effect before washing. As described above, the invention can provide a fibrous structure having antimicrobial activity with excellent industrial washing durability and a production process thereof.

Although this invention has been described in connection with specific forms thereof, it will be appreciated that a wide variety of equivalents may be substituted for the specific components and elements described herein without departing from the spirit and scope of the invention as described in the appended claims.

What is claimed is:

1. A molded antimicrobial article comprising an infiltrated 2-pyridylthiol-1-oxide zinc which forms independent phases of about 0.01 μm or more in short diameter in the molded article.

2. A molded antimicrobial article according to claim 1 wherein the antimicrobial agent is pyridine based.

3. A molded antimicrobial article according to claim 1 wherein the antimicrobial agent has an inorganic property/organic property value of about 0.3 to about 1.4.

4. A molded antimicrobial article according to claim 1 wherein the molecular weight of the antimicrobial agent is about 200 to about 700.

5. A molded antimicrobial article according to claim 1 wherein the molded article is fibers.

6. A molded antimicrobial article comprising an infiltrated 2-pyridylthiol-1-oxide zinc, wherein about 50% or more of the 2-pyridylthiol-1-oxide zinc is infiltrated to a depth of about 1 μm or more from the surface of the molded article.

7. A molded antimicrobial article comprising an infiltrated 2-pyridylthiol-1-oxide zinc, wherein about 30% or more of the 2-pyridylthiol-1-oxide zinc is infiltrated to a depth of about 2 μm or more from the surface of the molded article.

8. A molded antimicrobial article according to claim 1 wherein the pyridine based antimicrobial agent is 2-pyridylthiol-1-oxide zinc.

9. A molded antimicrobial article according to claim 5 wherein the pyridine based antimicrobial agent is infiltrated into the synthetic fibers.

10. A molded antimicrobial article according to claim 5 wherein the synthetic fibers are made from a polyester.

11. A molded antimicrobial article according to claim 5 wherein the synthetic fibers are colored by a disperse dye.

12. A molded antimicrobial article according to claim 5 wherein the synthetic fibers are colored by an acid dye.

13. A molded antimicrobial article according to claim 5 wherein the synthetic fibers are colored by a cationic dye.

14. A molded antimicrobial article according to claim 5 wherein the pyridine based antimicrobial agent is distributed substantially annularly near surfaces of the synthetic fibers inside the fibers.

15. A molded antimicrobial article according to claim 5 wherein the pyridine based antimicrobial agent is branched and is diffused from surfaces of the fibers to an inner portion thereof.

16. A molded antimicrobial article according to claim 1 wherein the microbiostatic activity value measured according to the microbe control evaluation method (standard testing method) specified by SEK (New Function Evaluation Conference for Fiber Goods) is about 2.2 or more after industrial washing of 12 minutes/time at 80° C.×50 times by a washing liquid containing a surfactant.

17. A process for producing a molded antimicrobial article comprising the steps of immersing a molded resin article in a liquid containing 2-pyridylthiol-1-oxide zinc with an average particle size of about 2 μm or less, and heat-treating the immersed article at about 90 to about 160° C.

18. A process for producing a molded antimicrobial article according to claim 17 wherein dry heat treatment is effected at about 160 to about 200° C. after heat-treatment in the liquid.

19. A process for producing a molded antimicrobial article comprising the steps of applying 2-pyridylthiol-1-oxide zinc with an average particle size of about 2 μm or less to a molded resin article by padding or spraying, and heat-treating the molded resin article at about 160 to about 200° C.

20. A process for producing a molded antimicrobial article according to claim 17 wherein the pyridine based antimicrobial agent is granulated in a colloidal state.

21. A process for producing a molded antimicrobial article according to claim 20 wherein the pyridine based antimicrobial agent is made colloidal by water and a formalin condensation product.

* * * * *

UNITED STATES PATENT AND TRADEMARK OFFICE
CERTIFICATE OF CORRECTION

PATENT NO. : 6,344,207
DATED : February 5, 2002
INVENTOR(S) : Goto et al.

It is certified that error appears in the above-identified patent and that said Letters Patent is hereby corrected as shown below:

Columns 3 and 4,
Below columns 3 and 4, please change "Table 2" to read -- Table 1 --

Column 12,
Lines 60 and 64, after "comprising" please delete "an"

Signed and Sealed this

Twenty-first Day of May, 2002

Attest:

Attesting Officer

JAMES E. ROGAN
Director of the United States Patent and Trademark Office